United States Patent [19]

Gardner

[11] B 3,985,817

[45] Oct. 12, 1976

[54] PREPARATION AND USE OF MAGNESIUM ACETYLENE COMPLEX

[75] Inventor: John Nicholson Gardner, Garrison, N.Y.

[73] Assignee: Hoffmann-La Roche Inc., Nutley, N.J.

[22] Filed: Apr. 15, 1974

[21] Appl. No.: 460,846

[44] Published under the second Trial Voluntary Protest Program on February 24, 1976 as document No. B 460,846.

Related U.S. Application Data

[63] Continuation-in-part of Ser. No. 402,544, Oct. 1, 1973, abandoned.

[52] U.S. Cl. ............................. 260/665 R; 260/638 R
[51] Int. Cl.$^2$ ................................................ C07F 3/02
[58] Field of Search ........................ 260/665 R, 665 G

[56] References Cited

UNITED STATES PATENTS

| | | | |
|---|---|---|---|
| 2,125,384 | 8/1938 | Macallum | 260/665 R X |
| 2,200,941 | 5/1940 | Vogt | 260/665 R |
| 2,938,932 | 5/1960 | Normant | 260/665 G |
| 3,441,621 | 4/1969 | Tedeschi | 260/665 R |
| 3,770,655 | 11/1973 | Vandenberg | 260/665 R |

OTHER PUBLICATIONS

Chemical Abstracts, v. 70, 86920e, (1969).

Chemical Abstracts, v. 41, 5043q, 5405g, (1947).

Chemical Abstracts, v. 64, 17623c, (1966).

Chemical Abstracts, v. 63, 17908e, (1965).

*Primary Examiner*—Helen M. S. Sneed
*Attorney, Agent, or Firm*—Samuel L. Welt; Bernard S. Leon; Richard A. Gaither

[57] ABSTRACT

Preparation of magnesium acetylene complex and its use in preparing ethynyl carbinols.

3 Claims, No Drawings

PREPARATION AND USE OF MAGNESIUM ACETYLENE COMPLEX

CROSS REFERENCE TO RELATED APPLICATIONS

This application is a continuation in part application of my earlier application Ser. No. 402,544 filed Oct. 1, 1973, Gardner now abandoned.

BACKGROUND OF THE INVENTION

In the past, ethynyl carbinols of the formula:

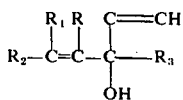

I wherein $R_1$ is lower alkyl, lower alkenyl or hydrogen; $R_2$ is hydrogen or a hydrocarbon having from 1 to 18 carbon atoms; $R_1$ and $R_2$ taken together with their attached carbon atom form a cyclic member selected from the group consisting of cyclo lower alkyl, or cyclo lower-alkenyl; and R and $R_3$ are lower alkyl, lower alkenyl or hydrogen;
have been formed by reacting a compound having the formula:

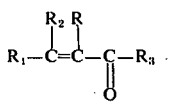

II wherein R, $R_1$, $R_2$ and $R_3$ are as above;
with sodium acetylide. See J.A.C.S. 57, p. 340, (1935) and J.A.C.S. 66, 1289, (1944). The use of sodium acetylide has proven disadvantageous since the yields of the compound of formula I have been low. In U.S. Pat. No. 2,425,201, Oroshnik, Aug. 5, 1947, the use of calcium acetylide for carrying out this process is disclosed. Furthermore, in Oroshnik et al. J.A.C.S. 71, 2062, (1949) the use of acetylides such as lithium acetylide, calcium acetylide and potassium acetylide for carrying out this process has been disclosed. However, these acetylides have proven to be very expensive. Furthermore, when these acetylides are utilized in this process, the compound of formula I is produced together with various side products and tars which are difficult to separate from the compound of formula I. Therefore, a more economical acetylide which will produce the compound of formula I in high yields without difficulty separable tars and side products has been long desired in the art.

The compound magnesium acetylide has been a compound that has been very hard to prepare owing to the difficulty of solubilizing magnesium and its acetylide in conventional solvents.

SUMMARY OF THE INVENTION

In accordance with this invention it has been discovered that when a magnesium acetylene complex is reacted with the compound of formula II in liquid ammonia, the compound of formula I is prepared in high yields without the substantial formation of difficulty separable side products and tars. Furthermore, in accordance with this invention, the compound of formula II can be reacted with a mixture containing both sodium acetylide and a magnesium acetylene complex where the mixture contains at least 5% by weight of a magnesium acetylene complex and at most 95% by weight of sodium acetylide to produce the compound of formula I in high yields without the substantial formation of by products and tars which are difficult to separate.

The inclusion in the reaction of at least 5% by weight of a magnesium acetylene complex in addition to sodium acetylide vastly improves the process of forming the compound of formula I by reacting an acetylene or an acetylide with the compound of formula II. The vast improvement in this process obtained by an addition of a small amount of a magnesium acetylene complex in addition to sodium acetylide over the process carried out utilizing sodium acetylide as the sole acetylide component is directly attributable to the addition of this complex. This can be seen by the fact that the yields of about 30% of the compound of formula I are obtained when sodium acetylide is utilized as the only acetylide component whereas yields of about 70% or greater are obtained when a small amount of the magnesium acetylene complex is added to this reaction mixture.

According to another embodiment of this invention, a process is provided for producing the magnesium acetylene complex. In accordance with this invention, this complex is formed when acetylene is reacted with magnesium in liquid ammonia in the presence of sodamide or sodium metal. If there is no sodamide or sodium metal present in this reaction, then this reaction will not take place and no complex will be produced.

DETAILED DESCRIPTION OF THE INVENTION

The lower alkyl groups which, in formulae I and II, are represented by the symbols R, $R_1$ and $R_3$ include, for example, straight or branched chain alkyl groups containing from 1 to 7 carbon atoms, such as methyl, ethyl, propyl, isopropyl, butyl, isobutyl, pentyl, hexyl, heptyl, etc. radicals. The lower alkenyl groups which in formulae I and II are represented by the symbols R, $R_1$ and $R_3$ include, for example, straight or branched chain alkenyl groups containing from 2 to 7 carbon atoms such as ethenyl, propenyl, 1-butenyl, 2-butenyl, 1-pentenyl, 2-pentenyl, etc. radicals.

The hydrocarbon radical $R_2$ in formulae I and II includes aliphatic, cycloaliphatic or aromatic hydrocarbon radicals, having from 1 to 18 carbon atoms. The aliphatic hydrocarbon radical may be saturated or unsaturated. Thus, for example, the hydrocarbon radical can be an alkyl group having from 1 to 18 carbon atoms, such as a methyl, ethyl, propyl, isopropyl, butyl, isobutyl, hexyl, octyl, decyl, undecyl, dodecyl, tetradecyl, pentadecyl, heptadecyl, octadecyl, etc. radical. Moreover, the hydrocarbon radical represented by the symbol $R_2$, indicates alkynyl or alkenyl groups, either straight or branched chain, having from 2 to 18 carbon atoms, such as ethynyl, propynyl, 1-butynyl, 2-butynyl, 1-pentynyl, 2-pentynyl, 2-methyl-2-pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, etc. radicals. The 4,8-dimethyl nonadien-3,7-yl group is exemplary of another hydrocarbon radical which is represented in formulae I and II by the symbol $R_2$.

When $R_2$ is aromatic containing hydrocarbon radical, this radical includes aromatic containing hydrocarbon radicals containing from 6 to 18 carbon atoms such as phenyl, lower alkyl substituted phenyl (which include o-tolyl, m-tolyl, etc.), naphthyl, phenyl substituted aliphatic hydrocarbon such as benzyl, phenethyl, etc. $R_2$ can be a cycloaliphatic hydrocarbon containing from 3 to 18 carbon atoms. Among the preferred cycloaliphatic radicals are the cyclo-lower alkyl radicals which contain from 3 to 7 carbon atoms such as cyclopropyl, cyclohexyl, etc. and the cyclo-lower alkenyl radical containing from 3 to 7 carbon atoms such as cyclohexenyl, and cycloheptenyl. The cycloaliphatic substituted aliphatic hydrocarbon radicals can contain from 4 to 18 atoms such as cyclohexyl-methyl, cyclohex-1-enylpenta-2,6-dien, etc.

Finally, taken together the symbols $R_1$ and $R_2$ of formulae I and II represent cycloalkyl groups, preferably cyclo-lower alkyl groups containing a ring having from 3 to 7 carbon atoms such as cyclopropyl, cyclobutyl, cyclopentyl, cyclohexyl, etc. groups or cycloalkenyl groups, preferably, cyclo-lower alkenyl groups containing a ring having from 3 to 7 carbon atoms, such as cyclopropenyl, cyclobutenyl, cyclopentenyl, cyclohexenyl, etc. groups. The cyclo-lower alkyl or cyclo-lower alkenyl groups can be substituted in one or more positions with a lower alkyl group. Generally, these cyclo-lower alkenyl or cyclo-lower alkyl groups contain from 3 to 18 carbon atoms.

In accordance with this invention, the magnesium acetylene complex is prepared by reacting magnesium with acetylene in liquid ammonia in the presence of sodium or sodamide. In carrying out this reaction, the sodium can be present in the mixture of magnesium and sodium in an amount of at least 5% by weight, based upon the total weight of the mixture. The sodium may be present either as metallic sodium or in the form of sodamide. If desired, any amount of sodium higher than 5% by weight, based upon the total weight of magnesium and sodium in the reaction mixture can be utilized depending upon the amount of the complex desired to be produced. This reaction is generally carried out with from about 5% by weight to 97% by weight of sodium, either in the form of sodium metal or as sodamide, based upon the weight of sodium and magnesium in the reaction medium. Amounts of sodium of from about 10% by weight to 80% by weight, based upon the weight of sodium and magnesium, in the reaction mixture, are preferred.

The reaction to produce magnesium acetylene complex is carried out in liquid ammonia as the solvent medium. In carrying out this reaction, acetylene is passed into the liquid ammonia reaction medium containing magnesium and sodium either in its metal or sodamide form. In carrying out this reaction, any combination of temperatures and pressures sufficient to keep the ammonia in a liquid state can be utilized. Generally, in carrying out this reaction, temperatures of from −100°C. to +100°C. with pressures of from about 15 lbs. per square inch absolute to 1,000 lbs. per inch absolute can be utilized.

Upon passing the acetylene gas into the reaction medium containing the sodium and magnesium, a mixture of sodium acetylide and the magnesium acetylene complex is formed. The complex forms as a precipitate while the major portion of the sodium acetylide remains dissolved in the liquid ammonia. Therefore, the magnesium acetylene complex can be recovered from the reaction medium by conventional means such as filtration.

The reaction of the compound of formula II with a mixture of sodium acetylide and the magnesium acetylene complex to form the compound of the formula I can take place in a liquid ammonia reaction medium. Therefore, the reaction medium resulting from the formation of the magnesium acetylene complex can be utilized to prepare the compound of formula I. Therefore, in preparing the compound of formula I, the compound of formula II can be added to the reaction medium utilized to form the magnesium acetylene complex and sodium acetylide without the necessity for separating or isolating the magnesium acetylene complex from the reaction medium.

In general, it has been discovered that the complex produced in accordance with this invention contains from about 1 part by weight of magnesium complexed with from about 0.9 to 2 parts by weight of acetylene.

In forming the magnesium acetylene complex, the magnesium can be reacted with acetylene in a liquid ammonia reaction medium in the presence of sodamide. Sodamide is the compound formed by sodium being combined with ammonia. The combination of sodium and ammonia is carried out by reacting metallic sodium and liquid ammonia in the presence of a ferric halide catalyst. Hence, the reaction between liquid ammonia and sodium to form sodamide can take place first in the liquid ammonia reaction medium followed by the addition of magnesium and acetylene to this medium to form the sodium acetylide and the magnesium acetylene complex.

In carrying out the reaction in accordance with this invention, it has been discovered that by the use of sodium either in the form of metallic sodium or sodamide, the reaction of acetylene and magnesium takes place to produce the magnesium acetylene complex. If sodium is not present in the reaction medium, one observes no reaction and no formation of the complex.

The reaction of the compound of formula II to form the compound of formula I can be carried out with the magnesium acetylene complex. Generally, it is preferred to carry out this reaction with a mixture of sodium acetylide and the magnesium acetylene complex. This is true since it has been found that only a small amount of this complex is necessary to increase the yield of the compound of formula I from that obtained by utilizing sodium acetylide alone. Therefore, in accordance with this invention, a mixture of such sodium acetylide and the magnesium acetylene complex is reacted with the compound of formula II to produce the compound of the formula I wherein the mixture contains at least 5% by weight of the magnesium acetylene complex. On the other hand, as pointed out hereinbefore, the magnesium acetylene complex can be utilized without the sodium acetylide. However, since this complex is far more expensive than sodium acetylide, it is best to utilize a mixture of both sodium acetylide and this complex in carrying out this reaction. Generally, mixtures of sodium acetylide and the magnesium acetylene complex containing from about 5% by weight to about 95% by weight of the complex are utilized in carrying out this reaction. However, it is generally preferred to utilize a mixture containing from about 20 to 90% of the complex.

In carrying out the reaction of the compound of formula II with a mixture of the magnesium acetylene complex and sodium acetylide in a liquid ammonia reaction medium, acetylene can be added to the reaction medium, if desired. It has been found that for best results, the presence of excess acetylene in the reaction medium is preferred. On the other hand, the reaction can take place without the presence of acetylene in the reaction medium. In addition to the liquid ammonia, inert organic solvents can be present in the reaction medium if desired. Among the preferred solvents are ethers such as diethyl ether, dioxane, tetrahydrofuran, etc.

In carrying out this reaction, any combination of temperature and pressure which is sufficient to keep the ammonia in a liquid state can be utilized. In carrying out this reaction, temperatures from about −100°C. to +100°C. with pressures of from about 15 p.s.i.a. to about 1000 p.s.i.a. can be utilized.

The following examples are illustrative but not limitative of the invention. In the examples, all temperatures are in degrees centigrade and the ether utilized is diethyl ether.

EXAMPLE 1

To 1500 ml. of liquid ammonia was added 0.2 g of anhydrous ferric chloride. To this mixture was added 60 g. of sodium which had been cut into pieces weighing 1 to 2 g. Each piece was allowed to dissolve and react to form sodium amide. After addition of the sodium was complete, 20 g. of magnesium turnings were added and the mixture was stirred for 18 hours. At the end of this period, the magnesium had dissolved and the mixture was pale gray in color. Acetylene was now passed through the mixture and in about one hour, the color turned to black.

200 ml. of diethyl ether was now added and a solution precooled to −10°C. of 210 g. methyl vinyl ketone in 600 ml. of diethyl ether was pumped in over 2.5 hours. The acetylene flow was then discontinued and the ammonia was evaporated by warming the flask with steam. When the mixture reached a temperature of 0°C. it was added slowly to 170 ml. of 98% by weight sulfuric acid and 2% water in 700 ml. of water while the acidic solution was cooled to maintain a temperature of less than 20°C. The diethyl ether layer was separated and the aqueous layer was extracted with 2 × 300 ml. of diethyl ether. The combined ethereal solutions were washed with 50 ml. of water, then with 50 ml. of water containing 10 ml. of saturated aqueous sodium bicarbonate solution and then with 50 ml. of water. The ethereal solution was dried over sodium sulfate and the diethyl ether removed by distillation of atmospheric pressure to a residue temperature of 90°C. The residue (237 g.) was distilled to yield 3-hydroxy-3-methylpent-1-en-4-yne (147g.) of assay 94%.

EXAMPLE 2

A flask is charged with about 6,000 ml. of liquid ammonia and 80 g. of magnesium is added. 240 g. of sodium is now introduced in four approximately equal portions and acetylene is passed through the solution between each addition at 6 to 8 cu. ft./hr. until the blue color is discharged. This entire process taken 1 to 2 hours. The acetylene flow is reduced to 1 to 2 cu. ft./hr. and the reaction mixture is stirred for 15 to 18 hours, during which time almost all the magnesium dissolves. 800 ml. of diethyl ether is now added and a pre-cooled (−10°C) solution of 840 g. of methyl vinyl ketone in 2,400 ml. of diethyl ether is pumped in over 1 hour. The mixture is stirred for 0.5 hour, the acetylene is shut off, and the ammonia is evaporated over 1 to 2 hours using steam to warm the flask. When the internal temperature reaches 0°C. the batch is dropped, over about 0.5 hour, onto a mixture of 1,900 g. of 98% by weight sulfuric acid and 2% by weight water and 1,900 g. of water which has been pre-cooled to −50°C. and to which 2,000 g. of ice has been added. The temperature of the acidic mixture does not exceed 10°C. The 3,000 ml. ether layer is then separated and the aqueous layer is extracted with 1,500 ml. of diethyl ether. The total diethyl ether solution is washed with 100 ml. of water, then with a mixture of 100 ml. of water and 20 ml. of saturated aqueous sodium bicarbonate solution, and finally with 100 ml. of water. The final wash has a pH of about 5. The ether solution is dried over anhydrous sodium sulfate and the ether is distilled off at atmospheric pressure to a residue temperature of ca. 75°C. The residue is distilled at reduced pressure via a 1ft. Vigreux column. The results of distillation are given in the following table:

| Fraction | B.P., °C | Pressure, mm. hg | Wt. in g. of 3-hydroxy -3-methyl pent-1-en-4-yne |
|---|---|---|---|
| 1 | 22–45 | 50–38 | 362 |
| 2 | 45–51 | 38 | 292 |
| 3 | 51–58 | 38–37 | 56 |
| Trap 1 | | | 11 |
| Trap 2 | | | 2 |
| Residue (Final Temp. 90°) | | | — |
| | | Total | 723 |
| Yield (on 100% methyl vinyl ketone = | $\frac{723}{1,152}$ | 100 = 62.8% | |

EXAMPLE 3

The flask is charged with about 6,000 ml. of liquid ammonia, and 80 g. of magnesium is added. 240 g. of sodium is introduced in four approximately equal portions and acetylene is passed through the solution between each addition at 6 to 8 cu. ft/hr. until the blue color is discharged. This entire process takes 1 to 2 hours. The acetylene flow is reduced to 1 to 2 cu. ft/hr. and the reaction mixture is stirred for 15–18 hrs during which time almost all the magnesium disolves. After this period, the reaction mixture was a white suspension. The reaction mixture was filtered to obtain an acetylene complex as a white solid which upon analysis was a mixture of a magnesium acetylene complex and sodium acetylide.

EXAMPLE 4

The flask is charged with about 1500 ml. of liquid ammonia and 45 g. of magnesium is added, 5 g. of sodium is now introduced and acetylene is passed through the solution at 6 to 8 cu. ft./hr. until the blue color is discharged. This process takes about 0.5 hour. The acetylene flow is reduced to 1 to 2 cu. ft./hr. and the reaction mixture is stirred for 15 to 18 hrs. during which time most of the magnesium dissolves. The resultant white suspension is decanted from the unreacted magnesium into centrifuge tubes and the magnesium acetylene complex is isolated by centrifugation. This complex is purified by suspending it at a temperature of −33°C. in liquid ammonia and again isolating it by centrifugation. The complex is then dried in vacuo over phosphorus pentoxide to produce a white to pale grey powder. Upon analysis, the complex contained about 38% by weight of magnesium and about 49% by weight of acetylene and 6.7% by weight of ammonia.

EXAMPLE 5

Sodium (30 g.) was dissolved in liquid ammonia (1,500 ml.) and acetylene was passed through the solution until the blue color was discharged. Magnesium turnings (10 g.) were added and the mixture was stirred for 18 hours while acetylene was passed slowly through it. During this period, almost all the magnesium dissolved. A solution of mesityloxide (10.7 g.) in diethyl ether (300 ml.) was cooled to −20° to −40°C. and was added to the reaction mixture over a period of about 5 minutes. The mixture was stirred for 5 hours, the ammonia was evaporated until the temperature of the residue reached −20°C., and the residue was dropped into a solution of sulfuric acid (200 ml.) in water (1,200 ml.) which was maintained at −5° to +15°C. The etheral layer was separated and the aqueous phase was extracted with two portions of diethyl ether (100 ml. each). The combined etheral extracts were washed with a mixture of aqueous saturated sodium bicarbonate solution (20 ml.) and saturated brine (80 ml.), then dried over sodium sulfate and the ether removed by distillation at atmospheric pressure. Distillation of the residue at 25°–34°C./3 mmHg yielded 3,5-dimethylhex-4-en-1-yn-3-ol (57.3 g.) and mesityl oxide (30.0 g.). The conversion of mesityl oxide was thus 72.0% and the yield of product 58.8%.

EXAMPLE 6

Sodium-magnesium acetylene complex was prepared as in Example 5 from liquid ammonia (1,500 ml.) sodium (60 g.) and magnesium turnings (20 g.). Diethyl ether (200 ml.) was added to the mixture followed by a solution, at −10°C. to −20°C., of crotonaldehyde (189 g.) in diethyl ether (600 ml.). The ammonia was evaporated and the residue was quenched and extracted as in Example 5. Distillation of the residue, after removal of the ether from the extracts, yielded hex-4-en-1-yn-3-ol (198 g; 77%), b.p. 60°–64°C./14-20 mmHg.

EXAMPLE 7

Sodium-magnesium acetylene complex was prepared as in Example 5 from sodium (15 g.), magnesium turnings (5 g.) and liquid ammonia (1,500 ml.). A solution, at +5°C. of benzalacetone (67 g.) in diethyl ether (250 ml.) was added over 15 minutes, the ammonia was evaporated and the reaction mixture quenched and extracted as in Example 5. After removal of the diethyl ether the residue was distilled, b.p. 101°–107°C./2 mmHg. The distillate comprised benzal acetone (7.6 g.) and 3-methyl-1-phenyl-pent-1-en-4-yn-3-ol (33.4 g.). The conversion of benzalacetone was thus 88.7% and the yield of product 46.4%.

I claim:

1. A process of producing a magnesium acetylene complex comprising reacting in liquid ammonia, magnesium and acetylene gas wherein the reaction medium contains from about 5 to 97% by weight of sodium in the form of sodium metal or combined with ammonia as sodamide, based upon the weight of sodium and magnesium in the reaction medium, said reaction taking place at a temperature of from −100°C. to +100°C. and a pressure of from about 15 psia to 1000 psia.

2. The process of claim 1 wherein the sodium is present as metallic sodium.

3. The process of claim 1 wherein the sodium is present as sodamide.

* * * * *